United States Patent
Poteet et al.

(10) Patent No.: US 9,013,686 B2
(45) Date of Patent: *Apr. 21, 2015

(54) CHEMICAL AND MOLECULAR IDENTIFICATION AND QUANTIFICATION SYSTEM UTILIZING ENHANCED PHOTOEMISSION SPECTROSCOPY

(71) Applicant: CDEX, Inc., Tucson, AZ (US)

(72) Inventors: Wade M. Poteet, Vail, AZ (US); Carey W. Starzinger, Benson, AZ (US); Jeffrey K. Brumfield, Romona, CA (US)

(73) Assignee: CDEX, Inc, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/498,302

(22) Filed: Sep. 26, 2014

(65) Prior Publication Data

US 2015/0009490 A1    Jan. 8, 2015

Related U.S. Application Data

(63) Continuation of application No. 13/673,270, filed on Nov. 9, 2012, now Pat. No. 8,848,173.

(60) Provisional application No. 61/628,979, filed on Nov. 10, 2011.

(51) Int. Cl.
| | | |
|---|---|---|
| *G01N 21/00* | (2006.01) | |
| *G01N 21/55* | (2014.01) | |
| *G01N 21/47* | (2006.01) | |
| *G01N 21/64* | (2006.01) | |
| *G01N 21/31* | (2006.01) | |
| *G01N 21/65* | (2006.01) | |
| *G01N 33/487* | (2006.01) | |

(52) U.S. Cl.
CPC ............ *G01N 21/55* (2013.01); *G01N 21/47* (2013.01); *G01N 21/64* (2013.01); *G01N 21/31* (2013.01); *G01N 21/65* (2013.01); *G01N 33/487* (2013.01); *G01N 2201/06113* (2013.01); *G01N 2201/067* (2013.01)

(58) Field of Classification Search
CPC ............ G01J 3/02; G01J 3/513; G01J 3/51; G01N 15/1459; G01N 21/65
USPC ......................................................... 356/73
See application file for complete search history.

(56) References Cited

U.S. PATENT DOCUMENTS

| | | | |
|---|---|---|---|
| 6,201,989 | B1 | 3/2001 | Whitehead et al. |
| 6,560,478 | B1 | 5/2003 | Alfano et al. |
| 2002/0004199 | A1 | 1/2002 | Hechinger |
| 2002/0131047 | A1 | 9/2002 | Zarrabian et al. |

(Continued)

*Primary Examiner* — Tarifur Chowdhury
*Assistant Examiner* — MD Rahman
(74) *Attorney, Agent, or Firm* — Millen, White, Zelano & Branigan, P.C.; William F. Nixon

(57) ABSTRACT

An enhanced photoemission spectroscopy (EPS) system uses at least three photoelectric detection processes to identify a substance or substances in a target. The target can be in a container, and the EPS system accounts for this in the identification process. The photoelectric detection processes include Raman scattering, fluorescence and spectral reflection. The EPS system uses all three processes to generate spectral data that is then combined to derive a target signature. The target signature is then compared to stored signature data to determine the substance or substances in the target.

18 Claims, 5 Drawing Sheets

(56) References Cited

U.S. PATENT DOCUMENTS

| | | |
|---|---|---|
| 2007/0064228 A1 | 3/2007 | Tartakovsky et al. |
| 2008/0154549 A1 | 6/2008 | Koshoubu et al. |
| 2009/0279088 A1 | 11/2009 | Fielden et al. |
| 2010/0208339 A1 | 8/2010 | Kleppe et al. |
| 2011/0040377 A1 | 2/2011 | Battis et al. |
| 2011/0290026 A1 | 12/2011 | Rice et al. |
| 2012/0056093 A1* | 3/2012 | Poteet et al. .................. 250/362 |
| 2013/0050696 A1 | 2/2013 | Antunovich et al. |

* cited by examiner

CHEMICAL AND MOLECULAR IDENTIFICATION AND QUANTIFICATION SYSTEM UTILIZING ENHANCED PHOTOEMISSION SPECTROSCOPY

This application is a continuation of U.S. patent application Ser. No. 13/673,270, filed Nov. 9, 2012.

FIELD OF THE INVENTION

The invention relates generally to the field of substance and material detection as used by an optical system, method and process that identifies specific molecules in a substance, and subsequently, determines their concentration in both single and multiple-substance mixtures. More specifically, the present invention relates to enhanced detection and identification capability using such systems and methods by utilizing enhanced photoemission spectroscopy.

DISCUSSION OF THE RELATED ART

Known substance verification systems may use spectral analysis to gather information about a substance of interest, and then compare the analysis results to spectral signatures. These systems may use a spectrometer to perform the analysis. The results may verify whether or not the substance of interest is a drug, compound and the like from signatures of these items. A device delivers a beam of light or other excitation energy to the substance to produce the spectral signature.

These systems, however, may not be able to identify an unknown substance, or a mixture of substances or compounds. Moreover, these systems are unable to perform their verification routines on mixtures or liquids inside standard and non-standard containers. Thus, personnel must remove the substance from its container and place it within a container suitable for analysis, for example, a clear container for analysis. Guesses also are made as to what the substance may be in order to verify against known spectral signatures. Such trial and error practice may lead to delays in properly identifying the substance or improper results.

Further, use of one type of spectrum analysis may conflict with the use of another. For example, one type of scattering may preclude simultaneous measurements using other spectral methods, which limits confidence in the results and efficiency.

SUMMARY OF THE INVENTION

The disclosed systems and methods allow identification and determination of unknown substances using enhanced photoemission spectroscopy. The disclosed embodiments identify specific molecules in a substance and determine their concentration. The disclosed embodiments measures these properties directly and also indirectly, such as through containers that are transparent or semi-transparent. The disclosed embodiments use the wavelength of the incident light to excite the molecules in the substance and then perform the disclosed methods to identify the target substance using the excitation energy created by the processes.

The disclosed embodiments also provide the capability of identifying individual components of a mixture or compound having more than one substance. The disclosed embodiments also may report the constituent molecular identification and concentration. Ancillary features include a method for weighing the material so that a volume of the different substances by weight can be determined when certain container parameters are introduced.

An example of the importance of this feature is an intravenous (IV) bag where a drug is introduced for total infusion of the bag's contents into a patient. If the drug concentration is correct, but the IV bag is not the appropriate volume, then an incorrect amount of total drug will be introduced into the patient. One possible implementation of this feature is to provide a weighing device in the sample compartment so that the IV bag's volume can be approximated by its weight, assuming that most of the volume is water (1 gram/cubic centimeter). In this way, the sample can be classified into the nearest commercial IV bag size, i.e., 50 ml, 500 ml, 1000 ml, 1.5 ml, 2000 ml, etc.

The disclosed systems, devices, and methods may apply to a wide spectrum of fields, such as pharmaceuticals. Pharmaceuticals in this sense includes prescription and non-prescription drugs, as well as parenteral mixtures, tablets, pills, powders, drug "cocktails," oncology admixtures, parenteral nutritional supplements, oral suspensions, narcotics, vitamin mixtures, electrolytes, diluents, other medications, contraceptives, antibiotics, analgesic drugs, antibiotics and the like. Such identification is important in the recovery and administration of the pharmaceuticals. Prior to leaving a lab or pharmacy, a quantity of material may be identified so that accidents and/or improper diversion are prevented. Unknown medication may be identified so that it can be disposed of properly.

Other materials identifiable by the disclosed embodiments include body fluids, such as blood, urine, saliva, other secretions, and the like. Samples of body fluids may be examined to determine levels of drugs or other chemicals.

The disclosed embodiments also may identify dangerous chemical compounds such as explosives, corrosives, solvents, toxic industrial chemicals, and the like. Identification of these materials may occur even when they are mixed with non-lethal or masking substances. Other dangerous compounds may include environmentally non-friendly substances such as water pollutants, air pollutants, toxic waste, landfill constituents, industrial emissions, sludge, chemical run-off materials, and the like.

The disclosed embodiments also may identify counterfeit pharmaceuticals and materials. These are materials put forth to match the group provided above, but, in fact, are not those materials. Counterfeit drugs are a rising problem, with placebos being substituted for the actual drugs. The disclosed embodiments also may be used to identify counterfeit perfumes, liquors, drinks, gasoline, industrial fluids, and the like.

Another application for the disclosed embodiments may include determining the potency of a drug or group of drugs over a period of time. The "decay" or potency degradation over time of the amount of a material within a combination of substances may be determined using the disclosed embodiments. The molecular analysis and determination may determine any breakdown of the target substance over time.

Application environments include, but are not limited to, hospitals, pharmacies, clinics, urgent care facilities, pharmaceutical manufacturing facilities (using raw materials and the finished product), supply chain product verification, extended care facilities, portable field measurements, airports, factories, landfills, toxic spill sites, repair shops, beverage dispensing locations, and the like.

The containers discussed below may be transparent or semi-transparent. For example, the preferred container may pass wavelengths of about 430 nm to 929 nm of light up to an attenuation factor between 75% to 95%. Examples includes, but are not limited to, clear glass vials, brown glass vials, syringes of any FDA-approved plastic material, IV bags of any manufacture, glass jugs, plastic jugs, drinking water containers, perfume bottles, liquor/beer bottles, soda/energy drink/sports drink containers, explosive wrapping materials, and the like.

BRIEF DESCRIPTION OF THE DRAWINGS

The accompanying drawings are included to provide further understanding of the invention and constitute a part of the specification. The drawings listed below illustrate embodiments of the invention and, together with the description, serve to explain the principles of the invention, as disclosed by the claims and their equivalents.

DETAILED DESCRIPTION OF THE PREFERRED EMBODIMENTS

Figure 1:
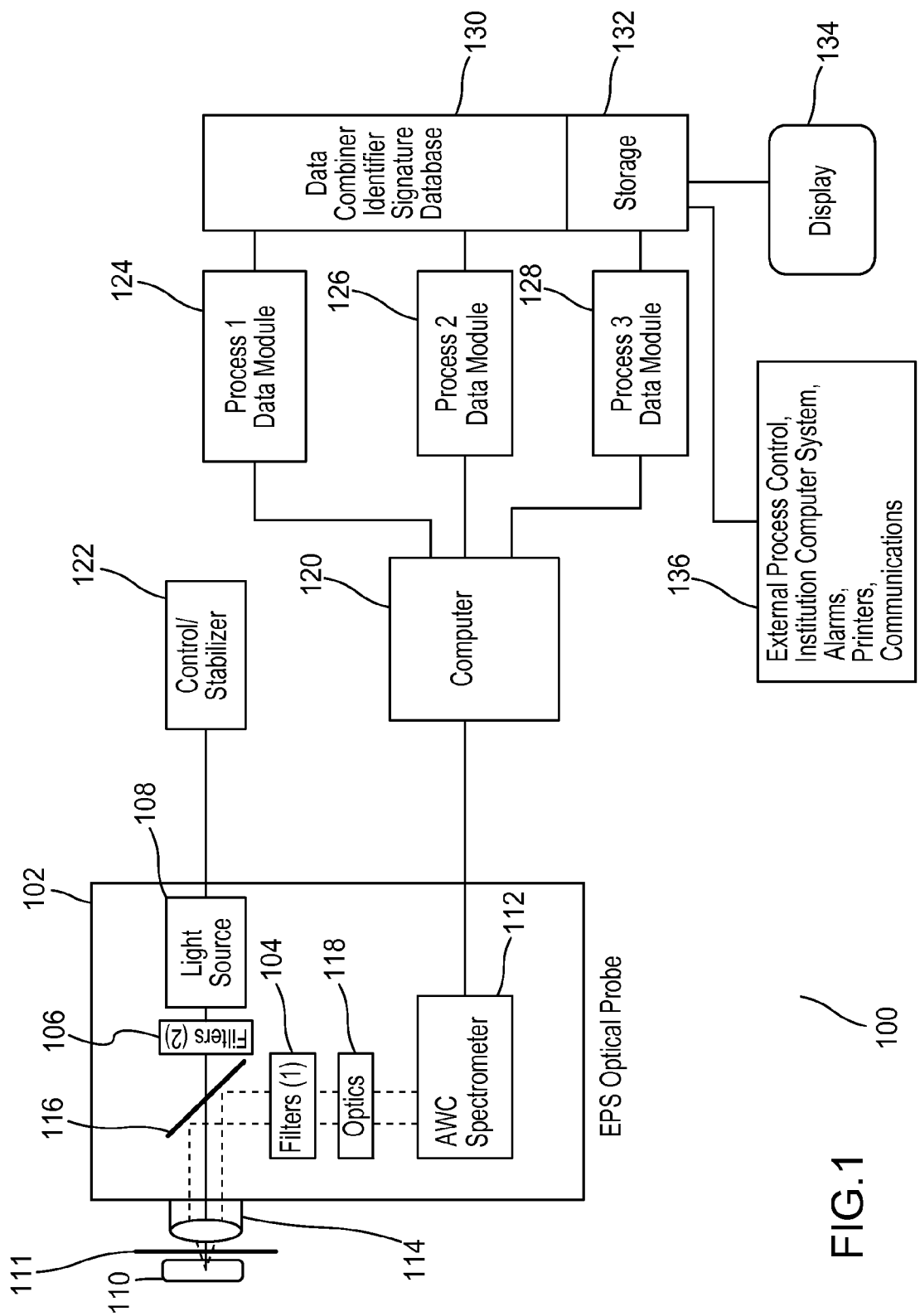
FIG. 1 illustrates an enhanced photoemission spectroscopy system including an optical probe according to the disclosed embodiments.

Aspects of the invention are disclosed in the accompanying description. Alternate embodiments of the present invention and their equivalents are devised without parting from the spirit or scope of the present invention. It should be noted that like elements disclosed below are indicated by like reference numbers in the drawings.

The disclosed embodiments include a molecular species identification and quantification system that includes an optical probe having a light source and spectroscopic detection device, a data storage system, a data manipulation module, and a computer interface including a digital processor. The disclosed system includes a unique configuration that allows novel data manipulation to provide improved results in substance identification.

The optical probe is configured to illuminate a sample of a substance and then gather photoemission or spectral reflection light components from the sample. The resulting data set is stored and analyzed to yield information related to three distinct processes that analyze the reflected energy to identify and quantify molecular species. The data also may provide general optical properties of the sample substance. The result of the analysis is compared to the stored database of molecular properties to allow determination of species and quantification.

The disclosed system provides several unique and nonobvious features. For example, the disclosed system provides an optical probe physical arrangement to optimize success in determining molecular species and concentration. The disclosed system also allows modularization of the physical configuration to adapt to a wide variety of measurement scenarios. The disclosed system incorporates utilization of data from three processes that occur when a sample is illuminated in the manner disclosed below. The disclosed system also implements data analysis methods that optimize precision and accuracy of the disclosed processes. Further, methods are provided that determine the optical transmission of sample containers simultaneously with the primary optical measurements, and measures all sample states—solid, liquid, powder and gaseous as well as the transition states between them.

FIG. 1 depicts an enhanced photoemission spectroscopy (EPS) system 100 according to the disclosed embodiments. EPS system 100 may be a hand-held device, or, alternatively, may be a desktop device. Components recited below may reside at different locations and exchange data over a wired or wireless network. System 100 includes a spectrum analysis module that processes the Raman scattered light into discrete Raman bands of interest, detects the presence of signal energy in each of the Raman bands, and produces a digital signal that is representative of the signal energy present in each of the Raman bands. The digital signal processing module of system 100 is adapted to perform a Raman analysis of the sample substance using the information from each of the Raman bands.

System 100 includes EPS optical probe 102. Optical probe 102 is configured for balanced performance for three simultaneous photoelectric processes. These processes include Stokes Raman scattering, fluorescence, and spectral surface reflectance. This configuration differs from conventional optical probe arrangements that involve configurations optimized for one optical process only. Other processes in a conventional arrangement are deliberately suppressed as much as practical. For example, Raman detection probes may be designed and configured to suppress as much fluorescence as possible so that weak Raman spectra can be detected effectively. The disclosed embodiments, in contrast, utilize each of the photoelectric processes simultaneously.

Optical probe 102 uses optical spectral filters 104 and 106. Optical filters 104 and 106 are chosen to allow a sizeable fraction of the Raman excitation wavelength from the excitation light source 108 reflected from sample 110 to the amplitude and wavelength calibrated (AWC) spectrometer 112. This feature utilizes the energy returned by the Raman excitation peak in the spectrum as part of the measurement for determining the absorption of a container 111 present between sample 110 and optical probe 102. A correction for sample container effects, therefore, is realized in the disclosed embodiments. No attempt to suppress fluorescent energy from sample 110 is made.

Optical probe 102 includes components configured to carry out the excitation and detection functions. Sample 110, however, resides outside optical probe 102, but is the subject of its activity. Sample 110 may be at a standoff distance such that system 100 is a hand-held device, and optical probe 102 aimed at the sample. Sample 110 may be solid, liquid or gas. Because the excitation and receiving light beam is sharply focused to about a 0.05 mm spot with sample 110, only about $1.25 \times 10^{-4}$ mm$^3$ of material of sample 110, for example, is needed to perform an effective measurement using optical probe 102. Other dimensions may be used for sample analysis along with any amount of material.

Lens assembly 114 is important to the probe design because of the requirement to balance the three photoelectric processes while not introducing large amounts of Raman spectral components from the container 111 into the return light entering spectrometer 112. A medium focal length lens is used to assure that any container contribution to the overall return spectrum is minimized relative to the sample spectrum. If the optics focal length is too short, then the sample container wall will be in focus or nearly so, and the container's photoelectric spectrum can dominate the return energy. If the optics focal length is too long, then the focus of the illuminating energy source falls outside the sample inside the container, and the substance of interest has a low probability of returning a useful spectrum.

For example, the container 111 is substantially out of focus, thus making that contribution to the return Raman energy small relative to the sample Raman energy return. Energy from fluorescence and spectral reflection benefit from this lens arrangement because the container contributions to these two photoelectric processes are minimized as well.

Beamsplitter 116 also is included in optical probe 102. Beamsplitter 116 assures that the optical axes of light source 108 and AWC spectrometer 112 are co-aligned. Other arrangements do not allow the minimum sample volume to be realized because the source and return optical beams would be viewing different portions of the sample volume.

Filter, or a set of optical filters, 104 is adjusted to provide saturation of the return excitation wavelength component of the EPS process light source 108 at the maximum integration time expected for AWC spectrometer 112. The Raman excitation wavelength returned from sample 110 must be of sufficient amplitude to allow sample container optical transmission determination, but not be so strong as to saturate the particular pixels in the AWC spectrometer 112 where this excitation wavelength falls.

Optical probe 102 includes optics 118. Collimation of the optical beam is desirable for proper transmission of wavelengths through optical filter, or filters, 104. Optics 118 are introduced to accomplish this feature and to couple the return energy from sample 110 to AWC spectrometer 112 in an efficient manner.

AWC spectrometer 112 (AWC also may mean amplitude and wavelength corrected) serves an important role in optical probe 102. AWC spectrometer 112 may be temperature-controlled to values achieved by thermoelectric coolers, typically 0° C. to −40° C., using a thermoelectric cooler to provide amplitude accuracy to 1% or better over one year of continuous operation. This value is derived from actual measurement of four spectrometers utilizing this technique.

AWC spectrometer 112 is important to the transfer of data from one sample of the disclosed invention to another, for example in a production environment where multiple units are to be utilized in a number of hospitals, industrial settings or customer facilities. Without this amplitude and wavelength calibration feature, it may not be possible to transfer a master database of signatures from one machine to another or to update all databases because the measured spectra would not otherwise align so that identification and quantification of materials can take place.

AWC spectrometer 112 includes a flash memory that allows storage of light source wavelength information. Spectral information provided by the AWC spectrometer 112 to computer 120 is generated in a format that relates each pixel in the detector array of AWC spectrometer 112 to the stored light source spectral information. This feature enables establishing a continuous wavelength calibration for the desired spectrum presented to computer 120.

Optical probe 102 also includes filter 106. Even if a laser is used as a light source 108, optical probe 102 may limit the spectral bandwidth to provide sufficient Raman narrow-band excitation. The spectral bandwidth, however, should not be so narrow that fluorescence and spectral reflection are totally masked or suppressed.

Light source 108 provides a narrow band of wavelengths, such as a laser, but this specific feature is not required. Sufficient energy should be provided by light source 108 to excite the Stokes Raman process as well as support the induced fluorescence. The spectral surface reflectance at the Raman excitation wavelength is at least $10^4$ times as energetic as the Raman itself, so a light source satisfying the requirements of producing measurable Raman spectral lines also provides sufficient energy returning to AWC spectrometer 112. Control/stabilizer 122 may be coupled to light source 108.

EPS system 100 also includes components not within optical probe 102. Computer 120 may include a processor, a memory and instructions to execute on the processor. Computer 120 may control the operations and data exchange of optical probe 102. Computer 120 also may provide spectrum storage. Computer 120 may be coupled to AWC spectrometer 112 of optical probe 102, but also may be coupled to other components.

Computer 120 is coupled to modules 124, 126 and 128. Modules 124, 126 and 128 may correspond to the three photoelectric processes disclosed above and below. For example, data module 124 may correspond to the Raman scattering process, data module 126 may correspond to the fluorescence analysis, and data module 128 may correspond to spectral surface reflectance. All three modules receive their data from computer 120. Data modules 124, 126 and 128 are coupled to data combiner 130 and storage 132. Data combiner 130 also may be an identifier and a signature database.

Modules 124-28 may be hardware, software, firmware, or combinations thereof, for executing the processes using the reflected energy from target 110. Modules 124-28 execute instructions to compare stored signature data for each of the applicable photoelectric processes: Raman scattering, fluorescence analysis and spectral surface reflectance. Data modules 124-28 also may access signature information for known containers so that they may subtract this information from the returned energy information processed by AWC spectrometer 112. Thus, containers may be accounted for and removed from the overall data so that sample 110 is properly identified. Preferably, data modules 124-28 include algorithms, as disclosed below, to give a high degree of certainty for matching the spectral information from all three processes to stored signature data.

The results from the analysis performed by data modules 124-28 and data combiner 130 may be shown on display 134. Display 134 may be any display known in the art to project information to a user. Alternatively, display 134 may be LEDs, or other indicators, to provide visual information to a user. Preferably, display 134 is a LCD display. The information displayed can also be made available to a local database, such as a hospital electronic medical record system for archiving, real-time verification of proper medication dosage, and tracking of patient medication history. Additionally, a pharmacy technician's or pharmacist's performance in compounding pharmaceuticals can be recorded and tracked for evaluation by hospital personnel. Results also may be sent to external process control 136, wherein various features are provided, such as alarms, printers, communications, adapters and the like.

As disclosed above, system 100 identified and quantifies molecular and chemical compounds using Enhanced Photoemission Spectroscopy, or EPS. EPS utilizes at least three different kinds of light interactions with molecular structures. Preferably, the disclosed embodiments use three different light interactions, which correspond to modules 124-28. Additional modules may be added to system 100 for additional light interaction analysis implemented.

One type of interaction used in the disclosed processes is fluorescence. Fluorescence is the emission of light by a substance having electrons that absorb light at a different wavelength. It may be a form of luminescence. As used above, the emitted light is longer in wavelength than the incident light, and, therefore, also is lower in energy than the incident light. When the absorbed light is very intense, such as produced by a laser, it is possible for one electron to absorb two photons. This two photon absorption may lead to emission of radiation having a shorter wavelength than the incident radiation. Thus, errors may occur using only a fluorescence process to identify sample 110, since many molecule combinations produce a similar fluorescence spectrum.

Another type of light interaction is Raman interaction, disclosed above. If the incident light is scattered from molecules in the target of interest, such as sample 110, the majority of the incident photons are elastically scattered, also known as Rayleigh scattering. This scattering produces no shift in the wavelength compared to the incident photons. The minority of the incident photons, such as about 1 in $10^7$, are inelastically scattered by an excitation with the scattered photons having a wavelength different from, and usually higher than, the wavelength of the incident photons. If the target is a gas, Raman scattering may occur with a change in vibrational or rotational energy of the target molecules. Preferably, the disclosed embodiments utilize the vibrational Raman scattering effect.

In fluorescence, the interaction of incident light with molecular structures involves absorption of photons precisely matching the difference in energy levels of electrons in the target molecules. This interaction results in re-emission after a certain resonance lifetime. The results of fluorescence and Raman scattering are similar in that a photon with a frequency different from that of the incident photon is produced and the molecule is brought to a higher or lower energy level. The difference between the two methods is that the Raman effect may take place for any frequency of the incident light from light source 108. The Raman effect may not be considered a resonant effect. A fluorescent peak may be anchored to a specific frequency, but a Raman peak maintains a constant separation from the excitation frequency.

There may be two types of Raman scattering: Stokes and anti-Stokes. In Raman scattering, the effect detected by EPS system 100 relates to the absorption and subsequent emission that occurs through an intermediate quantum (vibrational state) of a material. No energy exchange may occur between the incident photons and the molecules. Thus, there is no Raman wavelength shift. Alternatively, energy exchanges may occur between the incident photons and the vibrational states of the molecules, which leads to Raman interaction. The energy differences are equal to the differences of the vibrational and rotational energy levels of the molecule.

Stokes scattering may occur if the molecules absorb energy. Material within target 110 absorbs energy and the emitted photon has a lower energy value that the absorbed photon. The resulting photons of lower energy generate a Stokes emission line longer in wavelength than the incident photons. If the molecules lose energy, then this effect is known as anti-Stokes scattering and incident photons are shifted to a shorter wavelength than the incident photons, thus generating an anti-Stokes line. The material within target 110 loses energy and the emitted photon has a higher energy value that the absorbed photon. The energy difference between the absorbed and emitted photon corresponds to the energy difference between two resonant states of the material within target 110 and is independent of the absolute energy of the photon.

Because of considerations involving the relative number of molecules occupying various vibrational states and using the Boltzmann distribution of molecules in thermal equilibrium, it may be shown that lower energy states will have more molecules in them than will higher, or excited, energy states. Thus, the Stokes spectrum will be more intense than the anti-Stokes spectrum, and usually is the one of choice for molecular species identification in this invention.

The Raman effect is used by the disclosed embodiments for materials analysis. The spectrum of the Raman-scattered light depends on the molecular constituents present in target 110, and their state. The reflected spectrum is used for material identification and analysis by data module 124 within system 100. The spectral analysis may be used on gases, liquids, solids and combinations thereof. The Raman spectroscopy process may be particularly effective for biological organisms and human tissue.

Another possible interaction with incident light with a target is spectral reflection, or the absorption of certain wavelengths by the material and the reflection of others. This effect gives rise to the "colors" that are observed for different materials. The primary wavelength reflected is what is referred to as the color of a target. This reflected band of wavelengths can be used in addition to fluorescence and Raman scattering for verification of a material's identity or at least general typing of the target substance.

The disclosed embodiments implement EPS processing to utilize the data fusion of all three processes disclosed above to determine factors about the target substance, shown as sample 110. The disclosed processes may determine the specific molecule, the concentration of that molecule in a target or mixture, and the separation of constituents in a multi-molecular mixture. Additionally, the data produced in this method allow the effects of a transparent intermediate material, such as a container or wrapper, to be accounted for and, thus, eliminated as a source of extraneous return information from the identification/concentration determining process.

As noted above, conventional methods for determining molecular species and concentration go to considerable lengths to reject any fluorescence information from return spectra when performing Raman measurements. Further, Raman features in the data are carefully filtered out or removed when a purely fluorescence measurement is made. Spectral reflectance measurements alone do not make use of either fluorescent or Raman components present in the target's spectrum.

As noted, the components of EPS system 100 may provide features to improve the identification of substances and materials. System 100 may determine quantities and concentrations of the molecular structures present in sample 110. For example, light source 108 may be a laser operating at or near 785 nm wavelength to provide incident photons to the target. This provides a reasonable Raman response while also allowing a measureable fluorescent response and spectral reflection from the target. Preferably, light source 108 operates within a wavelength range of 500 nm to 850 nm.

System 100 also includes AWC spectrometer 112 for measuring the return spectrum from the target, or sample 110. Spectrometer 112 may be a stable spectrometer set to integrate for a specific period of time. Wavelength and amplitude of this spectrometer are accurately calibrated so that data and/or spectral signatures obtained with one device can be faithfully transferred to another device; thus multiple devices can utilize a common database for material identification and quantification. The output from spectrometer 112 is converted to voltages that represent the amplitude of the measured light at each wavelength within the spectrometer's operating range. This voltage is converted to a digital signal for storage and analysis in computer 120. The EPS data stored are subjected to analysis by the processor section of system 100 for concentration as disclosed in the following flowcharts. "Stored" may refer to storing the information in the analysis computer's storage medium, such as mass magnetic storage, mass optical storage, solid state memory, and the like.

Figure 2:
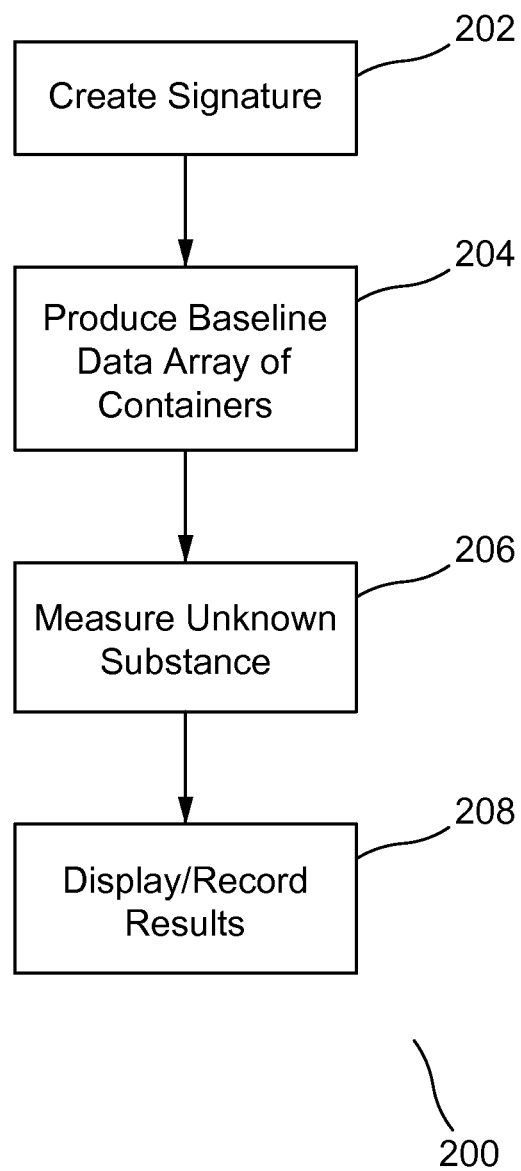
FIG. 2 illustrates a flowchart for determining the quantities and concentration of molecular structures according to the disclosed embodiments.

FIG. 2 depicts a flowchart 200 for determining the quantities and concentration of molecular structures according to the disclosed embodiments. Flowchart 200 provides an overview of more detailed steps disclosed in FIGS. 3-5. The steps shown in flowchart 200 may be performed by the components of EPS system 100 shown in FIG. 1. Additional components, however, may be implemented as needed, and the disclosed flowcharts are not limited to the configuration shown above.

Step 202 executes by creating a "signature" of an unknown substance from measurements of that substance to establish the signature database for future comparison to the spectra of unknown substances being measured. Step 204 executes by producing a baseline data array of "containers" that are likely to be used through which the unknown substance will be viewed. This step may be executed for each type of container possibly used with sample 110 as a target.

Step 206 executes by measuring the unknown substance. Step 208 executes by displaying or recording the results for viewing, reporting, further analysis, archiving and the like.

Figure 3:
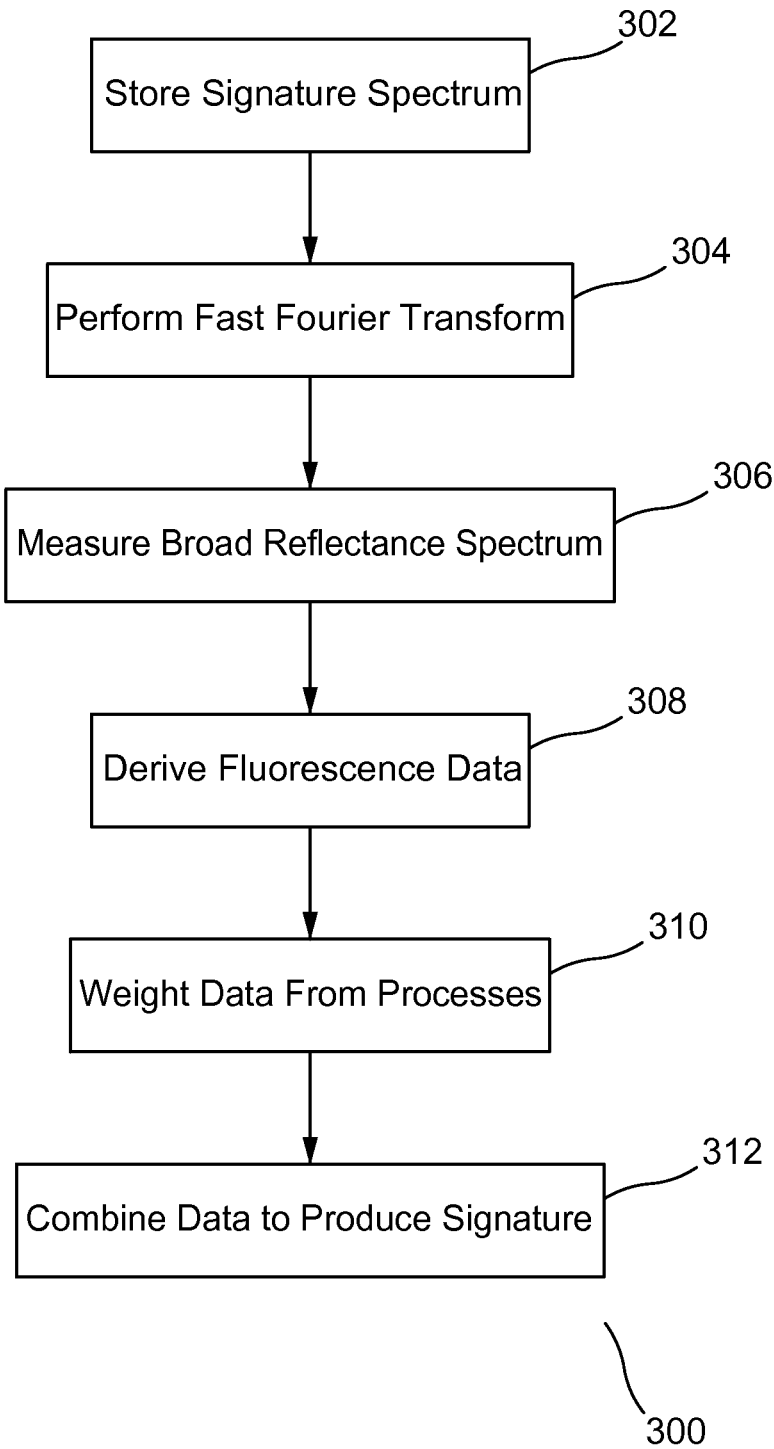
FIG. 3 illustrates a flowchart for creating signatures according to the disclosed embodiments.

FIG. 3 depicts a flowchart 300 that further discloses step 202 of FIG. 2 for creating signatures according to the disclosed embodiments. Step 302 executes by storing signature spectrum as both wavelength versus amplitude, and Raman shift versus amplitude. Step 304 executes by performing Fast Fourier Transform on this data, and storing the transformed results. Specific Fast Fourier Transform coefficients may be utilized in both the identification and quantification processes. Further, "peak analysis" routines unique to this invention are applied to the Raman data and then stored.

Step 306 executes by measuring the broad reflectance spectrum, or spectral reflection, using spectral software routines. Step 308 executes by deriving fluorescence data from the coefficients and curve flattening of the spectrum normalization routines. Step 310 executes by weighting the stored data from the three processes. Step 312 executes by combining this data to produce a "signature" for later comparison with an unknown substance for a possible match.

Figure 4:
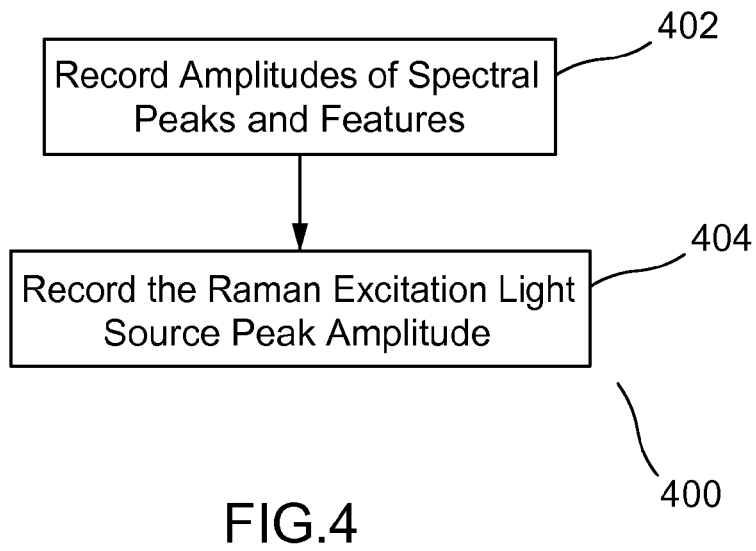
FIG. 4 illustrates a flowchart to produce a baseline array of containers according to the disclosed embodiments.

FIG. 4 depicts a flowchart 400 that further disclosed step 204 of FIG. 2 to produce a baseline array of containers according to the disclosed embodiments. Step 402 executes by recording the amplitudes of spectral peaks and features found in the corrected spectra obtained from fluorescence and Raman scattering. This step may be performed for each substance in the database. Step 404 executes by recording the Raman excitation light source peak amplitude that appears in the spectra for each substance in the database. Subsequent peak values of this Raman excitation amplitude are proportional to the absorption of the "container" and may be used to adjust for the effects of that container in the quantification process.

Figure 5:
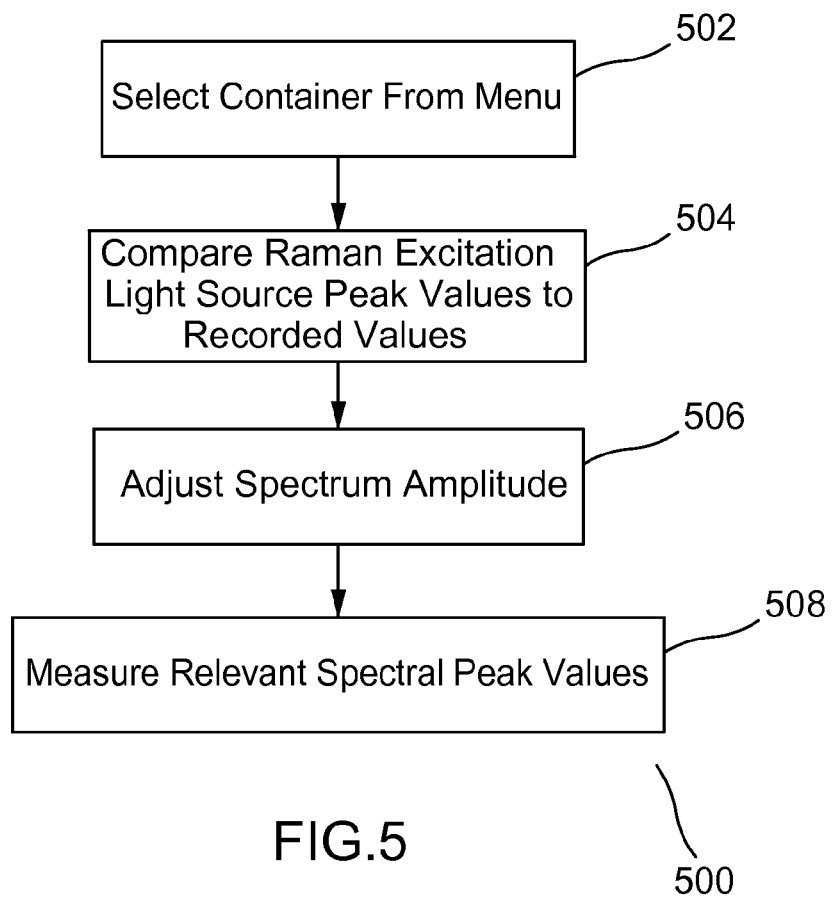
FIG. 5 illustrates a flowchart for measuring the unknown substance according to the disclosed embodiments.

FIG. 5 depicts a flowchart 500 for measuring the unknown substance as disclosed in step 206 in FIG. 2 according to the disclosed embodiments. Step 502 executes by selecting the appropriate container type from a menu. Step 504 executes by comparing the Raman excitation light source peak values to the recorded values of the baseline container Raman light source peak values. Step 506 executes by adjusting the spectrum amplitude to reflect the ratio from the comparison above. Step 508 executes by measuring the relevant spectral peak values by executed software to determine concentration values using polynomial regression software routines.

Figure 6:
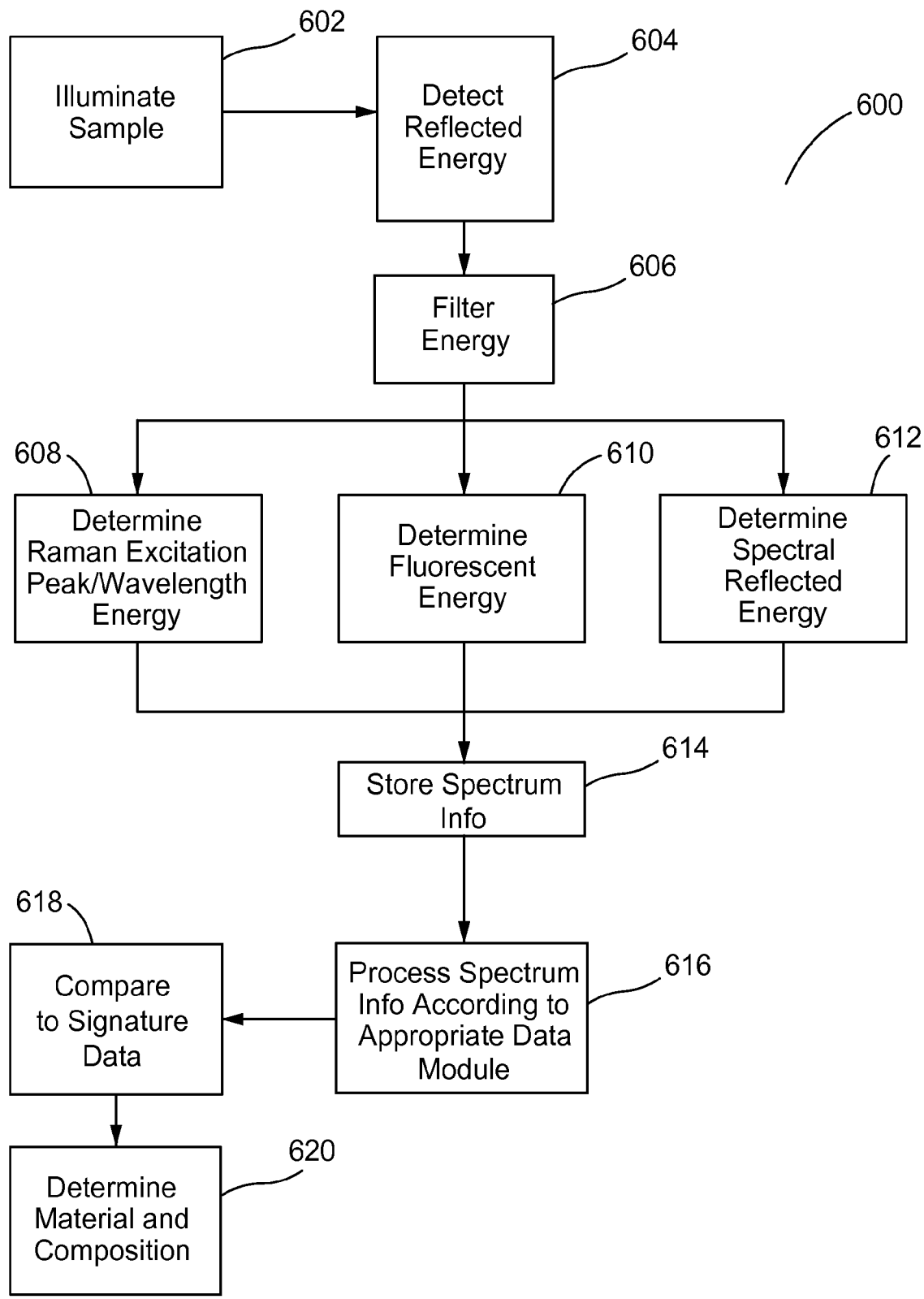
FIG. 6 illustrates a flowchart for using the enhanced photoemission spectroscopy system according to the disclosed embodiments.

FIG. 6 depicts a flowchart 600 for using the EPS system 100 according to the disclosed embodiments. Flowchart 600 represents the overall process using the flowcharts disclosed above. Flowchart 600 uses the three photoelectric processes disclosed above to identify and quantify target 110.

Step 602 executes by illuminate sample, or target, 110 with light energy from light source 108 of optical probe 102. The light energy hits sample 110 and reflects energy as well absorbs energy, as disclosed above. Step 604 executes by detecting this reflected energy as well as determining the energy reactions caused by the materials within sample 110. Step 606 executes by filtering this energy as desired.

Step 608 executes by determining the Raman excitation peak and/or wavelength of the returned light/energy using AWC spectrometer 112. Step 608 may use the processes disclosed above to determine these points. Step 610 executes by determining the fluorescent energy reflected from sample 110 using AWC spectrometer 112. Step 612 executes by determining the spectral reflected energy. Preferably, light source 108 transmits at a wavelength so that all three determinations may be made using the reflected energy from target 110. Optical probe 102, therefore, receives spectral information on target 110 applicable for all three processes.

Step 614 executes by storing the spectrum information on target 110 derived for all three processes. This information may be accessible by computer 120. Step 616 executes by processing the spectrum information according to the appropriate data module. In other words, data module 124 will receive the Raman excitation peak and scattering information. Data module 124 accesses signature data for substances of interest as well as that for possible containers. As noted above, a container may be selected by the user and, therefore, that signature data for the container is accessed. This process may be repeated for the other data modules for the other photoelectric processes.

Step 618 executes by comparing the spectrum information derived using all three processes to the applicable signature data. Matches are identified so that molecules within the material of target 110 can be determined. Step 620 executes by determining the materials within target 110 from the matched data as well as the composition of the materials using the matches from all three processes.

A further unique feature of this invention is the variable integration scheme incorporated in the actual measurement of an unknown or known substance. The AWC spectrometer's integration time is set to a fixed period that prevents saturation of the AWC spectrometer's output spectrum for common materials to be measured. A baseline algorithm is applied that "flattens" the spectrum and stores the result. Another spectrum is obtained and summed with the first spectrum and this process is repeated until a pre-set property of the spectrum is reached. The integration process then is complete and the summed spectra with flattened baselines are stored as the beginning point for the signature database.

Spectrum-flattening software routines create additional information as to the shape and amplitude of the fluorescent spectrum, and this information is stored for use as part of the eventual final substance signature. The spectral reflection information obtained from the spectrometer at wavelengths near the light excitation center wavelength and produced by the Gaussian rise and fall of the excitation light source energy profile are stored as well as part of the eventual final substance signature.

The disclosed embodiments also include a database, such as signature database 130, of common compounds for comparison and identification. The signatures stored in the database may include, but is not limited to, pharmaceuticals (prescriptive and non-prescriptive) as well as parenteral mixtures, tablets, pills, powders, drug "cocktails," oncology admixtures, parenteral nutritional supplements, oral suspensions, narcotics, vitamin mixtures, electrolytes, diluents, other medications, contraceptives, antibiotics, analgesic drugs, antibiotics and the like.

Other materials having signatures stored in the database include body fluids, such as blood, urine, saliva, other secretions, and the like. Samples of body fluids may be examined to determine levels of drugs or other chemicals.

The disclosed embodiments also may include signatures of chemical compounds such as explosives, corrosives, solvents, toxic industrial chemicals, and the like. Identification of these materials may occur even when they are mixed with non-lethal or masking substances. Other dangerous compounds may include environmentally non-friendly substances such as water pollutants, air pollutants, toxic waste, landfill constituents, industrial emissions, sludge, chemical run-off materials, and the like.

The disclosed embodiments also may include signatures of counterfeit pharmaceuticals and materials. These are materials put forth to match the group provided above, but, in fact, are not those materials. The disclosed embodiments also may include signatures for counterfeit perfumes, liquors, drinks, gasoline, industrial fluids, and the like.

As noted above, system 100 may measure through transparent containers, such as I.V. bags, syringes, bottles, vials, and the like. The relevant wavelength range of operation includes for the preferred embodiment includes, but is not limited to, 430 nm to 929 nm. Any "container" that passes these wavelengths of light up to an attenuation factor of 90% is used to provide the identification and concentration of substances using the processes described in this invention. Examples include, but are not limited to, clear glass vials, brown glass vials, syringes of any FDA approved plastic material, IV bags of any manufacture, glass jugs, plastic jugs, drinking water containers, perfume bottles, liquor bottles, and explosive wrapping materials.

System 100 also may provide volume of liquid samples by weight. System 100 may utilize a weighing system, along with software to enter weight data into the system's computer 120, to determine a volume by weight. This feature is viable for compounded pharmaceuticals because these liquids often possess a density at or near that of water. This feature also allows computer 120 to calculate the volume based on weight. For substances whose density varies from water by more than 10%, provisions in this embodiment are made for entering the substance's density so the volume by weight can be properly calculated by the system's software.

System 100 also may provide measurement results in real time. "Real time" has different meanings depending on the context of a particular measurement. For the purposes of system 100, "real time" means results are available to an operator within 5 seconds of completion of the spectral scan performed by the instrument and subsequent storage of that spectrum. In order to be maximally useful for the medical, explosive detection, and counterfeit determination applications, real time results are essential. First responders also must have real time results, because time is of the essence of their activities during emergency situations.

System 100 also may deconvolve multi-component mixtures of different chemical compounds to identify the separate components. Liquids and solids can contain two or more distinct substances, so the preferred embodiments have the capability of identifying and quantifying up to five (5) of these co-existing molecular constituents; its architecture does not limit it to five constituents, rather five is the present state of development of the software routines. Atomic constituents are also possibly individually identified by performing a software de-convolution of the features measured in the complex spectrum of the multi-constituent sample. An example of this is a total parenteral nutrition (TPN) mixture used in the medical field which may contain potassium, sodium, and other nutritional ingredients.

System 100 also may measure liquids, solids and powders. System 100 may measure the molecular constituents of a sample, through spectroscopy [EPS], in solids, liquids, and powders. Dense vapors are also included in the capabilities of this disclosed technology, for example, emissions from processes suspected of producing polluting substances. Pharmaceutical tablets which have industry standard coatings (usually for the purpose of potency preservation within the tablet) and whose coatings are penetrable by the wavelengths disclosed above, are another example of application of this technology. As long as the substance, in or out of a container, can be placed at the sensor portion of this invention, its molecular properties can be measured effectively.

System 100 also may measure complex taggants in liquids and solids placed into the material for identification of counterfeits. Taggants with specific measurable properties, including, but not limited to, fluorescent materials added to a product, have been used for many years to differentiate a manufacturer's product from a counterfeit. Potential counterfeiters can duplicate the taggant and thus circumvent detection of their counterfeit product. System 100 has the capability of measuring complex molecules mixed with a product, making it extremely difficult (and thus not profitable) for a counterfeiter to duplicate that complex molecule. Counterfeits can thus be easily identified and separated from a legitimate product using the disclosed invention.

Thus, as disclosed above, three processes may be used to determine light interactions to combine for a signature of known materials. The signatures are used to identify unknown substances as well as other information, as opposed to just verifying a substance. System 100 according to the disclosed embodiments is a more robust molecular identification system as a result.

It will be apparent to those skilled in the art that various modifications and variations can be made in the disclosed embodiments of the privacy card cover without departing from the spirit or scope of the invention. Thus, it is intended that the present invention covers the modifications and variations of the embodiments disclosed above provided that the modifications and variations come within the scope of any claims and their equivalents.

What is claimed is:

1. An enhanced photoemission spectroscopy (EPS) system to identify or quantify a substance comprising:
   an optical probe configured to perform at least three light or photoelectric processes, wherein the processes include Raman scattering detection, fluorescence detection and spectral surface reflectance detection to generate spectral data from each process, wherein the optical probe includes
   a light source to illuminate a target with sufficient energy transmitted at a wavelength to generate return energy to support the at least three processes, and
   an amplitude and wavelength calibrated (AWC) spectrometer to detect the return energy and to generate the spectral data;
   a computer coupled to the optical probe to access at least three data modules corresponding to each process, wherein the data modules are configured to analyze the spectral data from the at least three processes and derive a target signature for the target;

a signature database to store signature data of known substances, wherein the target signature is compared to the signature data; and a display to show results from the comparison between the target signature and the signature data.

2. The enhanced photoemission spectroscopy system of claim 1, wherein the light source is a laser.

3. The enhanced photoemission spectroscopy system of claim 2, wherein the laser generates a signal having a wavelength between 500 nm and 850 nm.

4. The enhanced photoemission spectroscopy system of claim 1, wherein the optical probe includes a lens assembly.

5. The enhanced photoemission spectroscopy system of claim 4, wherein the lens assembly includes lens having a medium focal length.

6. The enhanced photoemission spectroscopy system of claim 1, wherein the AWC spectrometer is temperature-controlled.

7. The enhanced photoemission spectroscopy system of claim 1, wherein data modules are configured to execute regression algorithms to process the spectral data.

8. A method to identify or quantify a substance using enhanced photoemission spectroscopy (EPS), the method comprising:

performing at least three light or photoelectric processes to generate reflected energy from the target substance, wherein the processes include Raman scattering detection, fluorescence detection and spectral surface reflectance detection, wherein the performing includes illuminating a target with sufficient energy transmitted at a wavelength from a light source to generate return energy to support the at least three processes, and detecting the return energy using an amplitude and wavelength calibrated (AWC) spectrometer;

processing the reflected energy from the at least three processes to generate spectral data for the target substance; and comparing a target signature derived from the spectral data to stored signature data to produce identification and concentration of an unknown substance or verification of a known substance.

9. The method of claim 8, wherein the Raman scattering detection includes determining a Raman excitation peak.

10. The method of claim 9, further comprising identifying a container of the target substance.

11. The method of claim 10, further comprising adjusting the spectral data of the reflected energy to account for the container.

12. The method of claim 8, further comprising weighting the spectral data from each process.

13. The method of claim 12, further comprising combining the weighted spectral data to generate the target signature.

14. A method for using an enhanced photoemission spectroscopy (EPS) system, the method comprising:

illuminating a target using light energy from an optical probe, wherein the optical probe includes a light source to transmit the light energy at a wavelength sufficient to generate reflected energy to perform Raman scattering detection, fluorescence detection and spectral surface reflectance detection;

detecting reflected energy from the target using the optical probe using an amplitude and wavelength calibrated (AWC) spectrometer;

determining a Raman excitation peak or wavelength and Raman scattering spectrum data from the reflected energy;

determining fluorescent spectrum data from the reflected energy;

determining spectral reflected spectrum data from the reflected energy;

processing the spectrum data from each of the three determining steps to generate a target signature for the target; and identifying at least one substance within the target according to the target signature.

15. The method of claim 14, wherein the processing step includes performing regression analysis on the spectrum data.

16. The method of claim 14, wherein the processing step includes weighting the spectrum data from each determining step.

17. The method of claim 14, further comprising displaying a result of the identifying step.

18. The method of claim 14, wherein the processing step includes adjusting the spectrum data in accordance with a container enclosing the target.

* * * * *